US00PP22197P2

(12) United States Plant Patent
Aardwegh

(10) Patent No.: US PP22,197 P2
(45) Date of Patent: Oct. 11, 2011

(54) *ECHINACEA* PLANT NAMED 'SUMMER SUN'

(50) Latin Name: ***Echinacea* hybrid**
Varietal Denomination: Summer Sun

(76) Inventor: Kees v.d. Aardwegh, Hillegom (NL)

( * ) Notice: Subject to any disclaimer, the term of this patent is extended or adjusted under 35 U.S.C. 154(b) by 115 days.

(21) Appl. No.: 12/590,868

(22) Filed: Nov. 16, 2009

(51) Int. Cl.
*A01H 5/00* (2006.01)

(52) U.S. Cl. ..... Plt./428

(58) Field of Classification Search ..... Plt./428
See application file for complete search history.

(56) References Cited

U.S. PATENT DOCUMENTS

PP10,050 P * 10/1997 Bergman ..... Plt./239
PP18,839 P2 * 5/2008 Korlipara ..... Plt./428
PP20,687 P2 * 1/2010 van Noor ..... Plt./428
PP21,811 P2 * 3/2011 van den Aardwegh ..... Plt./428
PP21,932 P2 * 5/2011 Korlipara ..... Plt./428
PP21,957 P2 * 5/2011 Korlipara ..... Plt./428

OTHER PUBLICATIONS

Anonymous. *Echinaceae* 'Summer Sun' accessed Dec. 18, 2010 available at: http://www.perennialresource.com/encyclopedia/view/?plant=1913 accessed Dec. 2010.*

UPOV ROM GTITM Computer Database, GTI Jouve Retrieval Software 2011/01 Citation for 'Summer Sun'.*

* cited by examiner

*Primary Examiner* — Wendy C Haas

(57) ABSTRACT

A new cultivar of hybrid *Echinacea*, 'Summer Sun', characterized by its inflorescences with ray florets that emerge yellow-orange in color and mature to orange-red in color, an upright habit with strong branched flower stems, and it vigorous growth habit.

2 Drawing Sheets

Botanical classification: *Echinacea* hybrid.
Variety denomination: 'Summer Sun'.

BACKGROUND OF THE INVENTION

The present Invention relates to a new and distinct cultivar of *Echinacea* of hybrid origin and will be referred to hereafter by its cultivar name, 'Summer Sun'. 'Summer Sun' represents a new purple coneflower, an herbaceous perennial grown for landscape use.

The Inventor discovered the new cultivar, 'Summer Sun', as a naturally occurring whole plant mutation in his trial field in June of 2008 in Hillegom, The Netherlands. The new cultivar was discovered as a single unique plant amongst a field of *Echinacea* seedlings from unknown parentage.

Asexual reproduction of the new cultivar was first accomplished by in vitro propagation in Rijswijk, The Netherlands in November 2008 under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Summer Sun' from other cultivars of *Echinacea* known to the Inventor.

1. 'Summer Sun' exhibits composite inflorescences with ray florets that emerge yellow-orange in color and mature to orange-red in color.
2. 'Summer Sun' exhibits an upright habit with strong, branched flower stems.
3. 'Summer Sun' exhibits a vigorous growth habit.

The new cultivar is unique from other cultivars of *Echinacea purpurea* known to the Inventor for its uniquely colored ray florets. The closest comparison cultivar is 'Arts Pride' (U.S. Plant Pat. No. 10,050), 'Arts Pride' differs primarily from 'Summer Sun' in having ray florets that mature to a lighter orange color, in having darker red-purple disk florets and in having stems that are less branched. 'Summer Sun' can also be compared to 'Tiki Torch' (U.S. Plant Pat. No. 18,839), 'Tiki Torch' is similar to 'Summer Sun' in having branched flower stems with orange colored ray florets, however 'Tiki Torch' differs from 'Summer Sun' in having ray florets that are lighter in color and more pink-orange rather than red-orange in color.

BRIEF DESCRIPTION OF THE DRAWING

The plants and plant parts in the accompanying photographs depict a two year-old plant of 'Summer Sun' as grown outdoors in a test garden in Hillegom, The Netherlands.

The photograph in FIG. 1 provides a side view of 'Summer Sun' in bloom.

Figure 1:
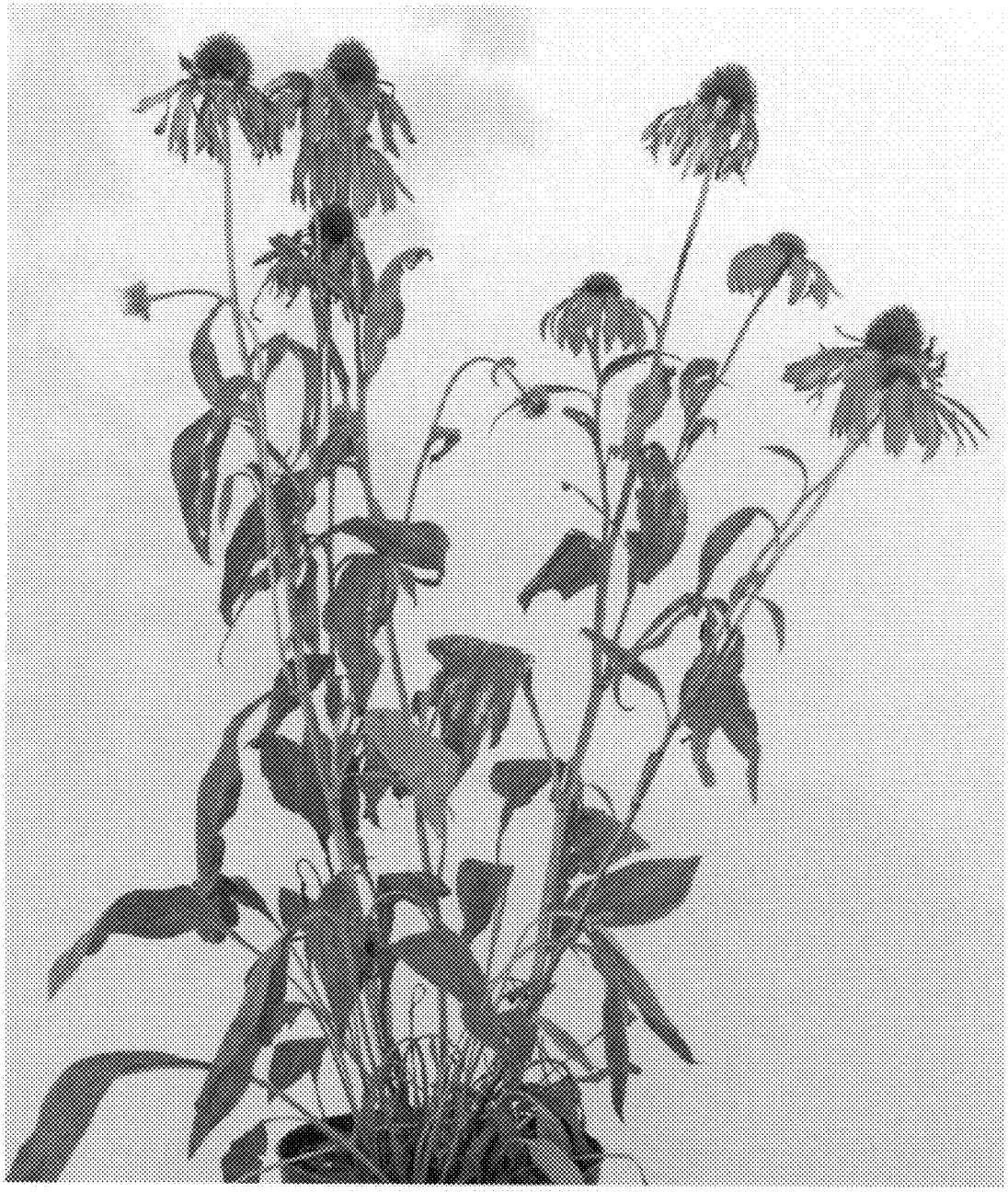
Figure 2:
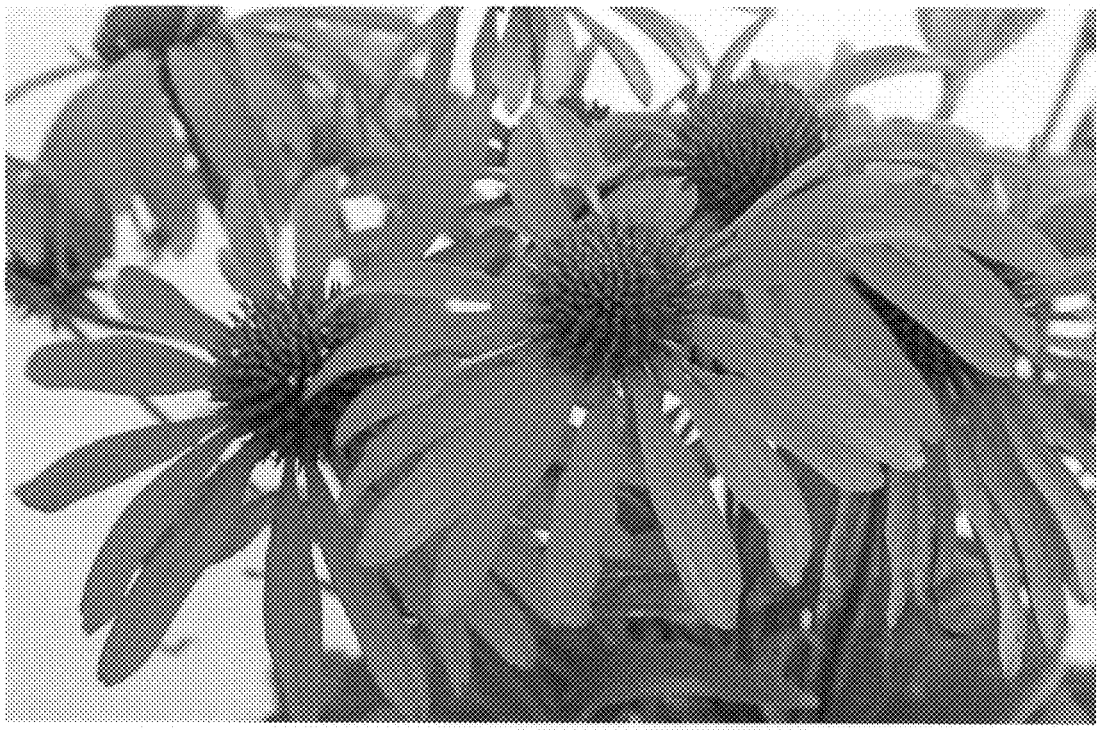

The photograph in FIG. 2 shows a close-up of the inflorescences of 'Summer Sun'.

Figure 3:
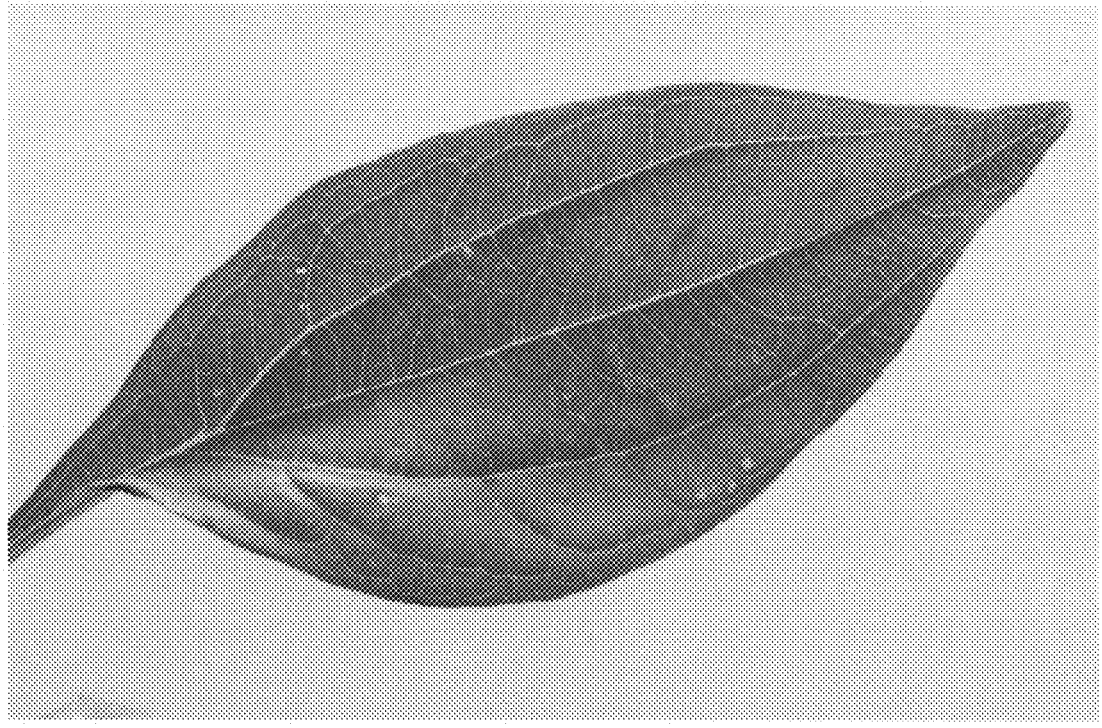

The photograph in FIG. 3 provides a close-up of a leaf of 'Summer Sun'. The Colors in the photograph may differ slightly from the color values cited in the detailed botanical description, which accurately describe the colors of the new *Echinacea.*

BOTANICAL DESCRIPTION OF THE PLANT

The following is a detailed description of two year-old plant of the new cultivar as grown outdoors in a test garden in Hillegom, The Netherlands. The plants were grown under average day temperatures of 12° to 30° C. and average night temperatures of 6° to 18° C. The phenotype of the new cultivar may vary with variations in environmental, climatic, and cultural conditions, as it has not been tested under all possible environmental conditions. The color determination is in accordance with The 2007 R.H.S. Colour Chart of the Royal Horticultural Society, London, England, except where general color terms of ordinary dictionary significance are used.

General description:

*Blooming period.*—Continuously from June to August.

*Plant habit.*—Herbaceous perennial, clump forming, upright.

*Height and spread.*—Reaches about 70 cm in height and 40 cm in spread.

*Cold hardiness.*—At least in U.S.D.A. Zones 4.

*Diseases resistance.*—Has shown no particular susceptibility or resistance.

*Root description.*—Fibrous.

Growth and propagation:

*Propagation.*—Division, vegetative stem cuttings, and tissue culture.

*Growth rate.*—Vigorous.

Stem description:

*Shape.*—Slightly oval, solid.

*Stem color.*—Ranges from 147B to 148B.

*Stem size.*—Main stem an average of 7 mm in diameter and 50 cm in length, lateral stems are an average of 5 mm in diameter and an average of 20 cm in height.

*Stem strength.*—Very strong.

*Stem aspect.*—Held upright.

*Stem surface.*—Moderately rough to touch and sparsely covered with short strigose hairs about 0.5 mm in length and 157D in color.

*Stem number.*—Average of 5 main stems per 2 year-old plant.

*Internode length.*—Average of 9.3 cm in length.

*Branching.*—1 to 2 lateral branches per main stem.

Foliage description:

*Leaf shape.*—Narrowly ovate.

*Leaf division.*—Simple.

*Leaf base.*—Attenuate.

*Leaf apex.*—Acute to narrowly acute.

*Leaf venation.*—Pinnate, 146D on upper and lower surface.

*Leaf margins.*—Slightly undulate.

*Leaf attachment.*—Petiolate.

*Leaf arrangement.*—Alternate.

*Leaf size.*—Average of 15.8 cm in length and 5.8 cm in width.

*Leaf color.*—Newly formed upper surface; 137B, newly formed lower surface; 137C to 137D, mature upper surface; between 137C to 139D and 147A, mature lower surface; 137B.

*Leaf surface.*—Upper surface is slightly glossy, lower surface is very slightly glossy, both surfaces are moderately covered with short strigose hairs about 0.3 mm in length and 157D in color.

*Petioles.*—Sulcate in shape, an average of 5.9 cm in length and 4 mm in width (petioles near top of stem are shorter), color upper surface; 144A to 144B in color surface is smooth and glossy.

Flower description:

*Type.*—Capitulum, heterogamous with ray florets around the head margin and disk florets in the center, forming a radiant head.

*Capitulum number.*—An average of 3 per stem.

*Lastingness of inflorescence.*—About 2 weeks.

*Capitulum size.*—Matures to about 6 cm in depth and 11.4 cm in diameter, disk is about 3.5 cm in diameter.

*Fragrance.*—Moderate, sweet-scented.

*Involucral bracts or phyllary.*—About 48 arranged in 3 overlapping rows, average of 9 mm in length and 3 mm in width, cuneate base, acute apex, narrowly ovate to lanceolate in shape, slightly curved towards peduncle, upper surface is 143A to 143B in color, lower surface is 137A to 137B in color, margins entire and densely covered with short strigose hairs about 0.3 mm in length and 157D in color, surface is dull and rough on both surfaces.

*Buds.*—Flatten globular in shape with disk florets nearly vertical at apex, up to 2.9 cm in diameter and 2.2 cm in height, color is between 143A and 145A with center 141A and 141B.

*Peduncle.*—Strong, terminal is an average of 14 cm in length and 4 mm in diameter with axillary peduncles an average of 11.1 cm in length and 4 mm in diameter, a color between 147B and 148B, surface is rough to touch and sparsely covered with short strigose hairs about 0.5 mm in length and 157D in color.

*Ray florets* (*sterile*).—Average of 21 in single row, narrow elliptic to narrowly obovate in shape, vertical ridges on both surfaces, about 5.9 cm in length and 1.2 cm in width, emarginate to praemorse apex, cuneate base, entire margin except apex, smooth and dull surface on both surfaces, held slightly downward when mature, color of upper surface when opening; N30B, color of lower surface when opening; 51A and 51C, color of upper surface when fully open; 45A and 42B near apex, color of lower surface when fully open; 59C and 59D, color of upper surface when fading; 179B with base 181A, color of lower surface when fully mature; 181C to 181D.

*Disk flowers* (*bisexual*).—Numerous, about 200, tubular in shape, fused into tube with upper 10% un-fused, arranged spirally on a narrowly triangular shaped receptacle; an average of 1.1 cm in height and 6 mm in diameter, 158D in color, an average 1.2 mm in height and 2.5 cm in width and 158D in color, apex is acute, fused base, entire margin, surface of upper surface and lower surface is smooth and glossy, color when opening and fully open upper and lower surface; 146C to 146D with apex a color between 146A and 147A.

*Disk spines.*—Average of 200, acicular in shape, acute apex, attenuate base, smooth and glossy surface, color is 53A at apex, 25A and N25B in mid region and 144D at base.

Reproductive organs (present on disk florets only):

*Gynoecium.*—Pistil; 1, an average of 8 mm in length, style; about 6 mm in length and 187C to 187D in color, stigma; decurrent and N186C in color, ovary; 157D in color.

*Androcoecium.*—Stamens; 5, filaments; 2 mm in length and 145C in color, anthers; basifixed, about 3 mm in length and 200A to 202A in color, pollen; moderate to high in quantity and 17A in color.

*Fruit/seed.*—No seed production has been observed.

It is claimed:

1. A new and distinct cultivar of *Echinacea* plant named 'Summer Sun' substantially as herein illustrated and described.

* * * * *